United States Patent [19]

Tanaka et al.

[11] Patent Number: 5,403,893
[45] Date of Patent: Apr. 4, 1995

[54] INTERPENETRATING-POLYMER NETWORK PHASE-TRANSITION GELS

[75] Inventors: Toyoichi Tanaka, Wellesley, Mass.; Franck Ilmain, St. Etienne, France; Etsuo Kokufuta, Tsukuba, Japan; Masahiko Annaka, Arlington, Mass.

[73] Assignee: Massachusetts Institute of Technology, Cambridge, Mass.

[21] Appl. No.: 150,557

[22] Filed: Nov. 10, 1993

Related U.S. Application Data

[63] Continuation of Ser. No. 720,187, Jun. 24, 1991, abandoned, which is a continuation of Ser. No. 648,563, Jan. 31, 1991, abandoned.

[51] Int. Cl.$^6$ ............................................. C08L 33/24
[52] U.S. Cl. ........................................ 525/218; 523/105; 524/521; 524/522; 525/129; 525/219
[58] Field of Search ............... 524/521, 522; 525/129, 525/218, 219; 523/105

[56] References Cited

U.S. PATENT DOCUMENTS

| 4,302,553 | 11/1981 | Frisch et al. | 525/28 |
| 4,732,930 | 3/1988 | Tanaka et al. | 524/742 |
| 5,100,933 | 3/1992 | Tanaka et al. | 523/300 |

FOREIGN PATENT DOCUMENTS

| 0347145 | of 1989 | European Pat. Off. |
| 0365011 | 4/1990 | European Pat. Off. |
| 0411621 | of 1991 | European Pat. Off. |
| 61-055180 | of 1986 | Japan |
| 3002211 | of 1991 | Japan |
| 3079608 | of 1991 | Japan |

OTHER PUBLICATIONS

Okano et al., *Journal of Controlled Release*, 11:255–265 (1990).
Katono et al., *Journal of Controlled Release*, 16:215–228 (1991).
Klenina et al., *Polymer Science*, 23(6):1439–1446 (1982).
Matsuo et al., *J. Chem. Phys.*, 89(3):1695–1703 (1988).
Mamada et al., *Macromolecules*, 23(5): 1517–1519 (1990).
Suzuki et al., *Nature*, 346: 345–347 (1990).
Amiya et al., *Macromolecules*, 20(5): 1162–1164 (1987).
Irie et al., *Macromolecules*, 19(10): 2476–2480 (1986).
Hirokawa et al., *J. Chem. Phys.*, 81(12): 6379–6380 (1984).
Ilavsky, M. *Macromolecules*, 15: 782–788 (1982).
Ohmine et al., *J. Chem. Phys.*, 77(11): 5725–5729 (1982).
Tanaka et al., *Science*, 218: 467–469 (1982).
Hrouz et al., *European Polymer Journal* 17: 361–366 (1981).
Tanaka, T., *Scientific American*, 244(1): 124–138 (1981).
Tanaka, T., et al., Scattering Techniques Applied to Supramolecular and Nonequilibrium Systems, Ed. Chen, Chu and Nossal, Plenum Pub. Corp. pp. 321–336 (1981).
Tanaka et al., *Phys. Rev. Lett.*, 45(20): 1636–1639 (1980).
Tanaka, T., *Phys. Rev. Lett.*, 40(12): 820–823 (1978).
Tanaka, et al., *Phys. Rev. Lett.*, 38(14): 771–774 (1977).

*Primary Examiner*—Paul R. Michl
*Assistant Examiner*—U. K. Rajguru
*Attorney, Agent, or Firm*—Choate, Hall & Stewart

[57] ABSTRACT

An interpenetrating gel and a method of forming an interpenetrating gel which undergoes a significantly large volume change in response to a physical or chemical stimululs is disclosed.

39 Claims, 5 Drawing Sheets

INTERPENETRATING-POLYMER NETWORK PHASE-TRANSITION GELS

GOVERNMENT SUPPORT

Support for at least some of the work described and claimed herein was provided under the terms of Contract No. DMR-8920401, awarded by the National Science Foundation. Therefore, the government has certain rights to subject matter claimed herein.

RELATED APPLICATIONS

This is a continuation of application Ser. No. 07/720,187, filed on Jun. 24, 1991, now abandoned, which is a Continuation of Ser. No. 07/648,563, filed Jan. 31, 1991, now abandoned.

BACKGROUND OF THE INVENTION

Gels can exhibit phase transition, or significantly large volume change, in response to variation of the surrounding conditions. For example, the fluids supporting a gel can be modified to cause a significantly large contraction or expansion of a gel such as by changing the pH, solvent composition, relative concentration of solvents, solvent temperature, or the ion concentration of the fluid.

However, phase transition of gels generally has been dependent upon generating an interaction between a gel polymer network, comprising a single polymer and a phase-transition-modifying agent, or upon intramolecular interactions between like-strands of the polymer network. Also, phase transition caused by changes in fluid temperature have heretofore been limited to significantly large contraction during an increase in temperature and, conversely, a significantly large expansion during a decrease in temperature.

SUMMARY OF THE INVENTION

The present invention relates to phase-transition gels and to methods of forming phase-transition gels which undergo a significantly large volume change at a desired phase-transition condition in response to a stimulus.

The invention is an interpenetrating polymer network gel that undergoes a phase transition in response to a specific stimulus. The interpenetrating polymer network is gelled with a liquid medium.

A method of forming a phase-transition gel which undergoes a significantly large volume change at a desired phase-transition condition in response to a stimulus includes forming an interpenetrating polymer network, having a first polymer and a second polymer interpenetrating the first polymer. The interpenetrating polymer network is designed to undergo a significantly large volume change in response to a chemical or physical stimulus. The interpenetrating polymer network forms a gel with a liquid medium.

This invention has many advantages and uses. Importantly, the gels of the present invention exhibit a significantly large increase in volume by increasing the temperature of the phase-transition gel and exhibit a significantly large contraction by lowering the temperature of the phase-transition gel. Also, the phase-transition gels of the present invention can exhibit a phase transition in response to hydrogen bonding between interpenetrating polymers of the gel.

Gels of the present invention can also be used for chemical separation. For example, components of a solution can be separated from a solution based upon hydrogen bonding, ionic interaction, van der Waals forces, hydrophobic interaction, and/or any other kind of chemical bond. The chemical bond can be between the component to be separated from the solution and any of the polymers of the interpenetrating polymer network, to thereby cause a phase transition of the polymer network and, consequently, cause a phase transition of the gel. Also, interaction between a component in a liquid medium within the interpenetrating polymer network and the interpenetrating polymer network can cause an interaction between the polymers of the interpenetrating polymer network which, in turn, causes a phase transition of the gel.

Whether the phase transition of the gel is caused by one or more of the polymers of the interpenetrating polymer network, the component can be separated from the solution by contraction of the gel during phase transition by entrapment of the component in the gel or by binding to the polymer network in the gel. Alternatively, small components can be separated from large components that pass through the gel by adjusting the pore size of the network to exclude large components. The pore size of the network is adjusted when the polymer network undergoes a phase transition. Consequently, gels of the present invention can be formed which trap specific compounds, including: potentially physiologically harmful agents, such as fat and cholesterol; microbial toxins; abnormally high levels of phosphate, sodium or potassium; etc.

Also, the gels of the present invention can be designed to release chemicals in response to exposure of the gel to a chemical trigger or a physical trigger which interacts with one or more of the polymers of the interpenetrating polymer network to thereby directly cause phase transition of the gel or to indirectly cause phase transition by initiating interaction between the polymers. Elimination of the chemical trigger can cause the phase transition of the gel to be reversed.

DETAILED DESCRIPTION OF THE INVENTION

The features and other details of the phase-transition gels and methods of forming the phase-transition gels of the invention will now be more particularly described and pointed out in the claims. It will be understood that the particular embodiments of the invention are shown by way of illustration and not as limitations of the invention. The principal features of this invention can be employed in various embodiments without departing from the scope of the invention.

"Phase-transition" of gels, as that term is used herein, means a significantly large volume change of gels between an expanded phase and a contracted phase or vice-versa. "Phase-transition gels," as that term is used herein, are gels which exhibit a phase transition at a phase-transition condition. The difference in volume between the expanded phase of phase-transition gels and the contracted phase of the phase-transition gels can be orders of magnitude. Examples of phase-transition gels are disclosed in Tanaka et al., U.S. Pat. No. 4,732,930 and U.S. patent application Ser. Nos. 07/425,788, 07/470,977 and 07/558,733, the teachings of which are incorporated herein by reference.

The phase-transition gels of the present invention undergo a significantly large volume change at a desired phase-transition condition in response to a stimulus. The phase-transition gel includes an interpenetrating polymer network gelled with a liquid medium.

A liquid medium is suitable if the interpenetrating polymer network can be gelled with the liquid medium to thereby form a phase-transition gel. Examples of suitable liquids include water, aqueous solutions, organic and inorganic liquids. The liquid medium also can be a solution or a mixture of liquids. An example of a suitable organic liquid is a dioxane.

In one embodiment, the interpenetrating polymer network of the present invention includes a first polymer and a second polymer, wherein the second polymer interpenetrates the first polymer. Suitable first and second polymers include polymers which can interact during exposure to a phase-transition condition to thereby cause a significantly large volume change of the gel. It is to be understood, however, that the interpenetrating polymer network can include more than two polymers. For example, additional polymers can be included which interpenetrate the first and/or second polymers.

The distinct polymers interpenetrate each other, in that strands of each polymer are maintained in relation to strands of at least one other polymer, whereby an interaction between the strands of the polymers causes a gel, formed of the polymers which are gelled with a liquid medium, to exhibit a phase transition between a contracted phase and expanded phase, and vice versa. In one embodiment, the polymers overlap each other, such as by being tangled within one another. In another embodiment, any one or more of the polymers can be crosslinked to form a network of interstices whereby the other polymers are distributed through the interstices of the network. In a particularly preferred embodiment, the interpenetrating polymer network is formed by first polymerizing and crosslinking a first monomer. Thereafter, a second monomer is disposed within the interstices formed by crosslinking of the polymerized first monomer. The second monomer is then polymerized and crosslinked, thereby forming interstices through with the strands of the first polymer extend.

In a preferred embodiment, the first and second polymers of the interpenetrating polymer network form a "polycomplex." "Polycomplex," as that term is used herein, means an interpenetrating polymer network which includes a first polymer and a second polymer interpenetrating with the first polymer, and wherein an interaction occurs between the first polymer and the second polymer sufficient to cause alignment between polymer strands of the first and second polymers in an amount sufficient to cause a significantly large volume change of the phase-transition gel "Polycomplexation," as that term is used herein, means alignment by interaction between strands of the first and second polymers in an amount sufficient to cause a discontinuous volume change of the phase-transition gel. Examples of the interactions which can occur between the first and second polymers of the interpenetrating polymer network include oxidizing, reducing, complexing, ionizing, chemically reacting van der Waals forces, hydrophobic interaction, hydrogen bonding and ionic interaction.

The polymers of the interpenetrating polymer network can comprise natural polymers, synthetic polymers, or cross-linked synthetic and natural polymers. Also, the polymers can be block copolymers. Examples of synthetic polymers include poly(N-isopropylacrylamide), poly(acrylamide), poly(acrylic acid), etc. In one embodiment, the interpenetrating polymer network includes poly(acrylic acid) as one polymer, poly(acrylamide) as another interpenetrating polymer, and water as the liquid medium. In another embodiment, the interpenetrating polymer network includes two interpenetrating polymers of poly(acrylic acid), and water as the liquid medium. In both embodiments, the phase transition can occur by polycomplexation due to hydrogen bonding between the interpenetrating polymers of the interpenetrating polymer network.

Examples of phase transition gels which are formed of interpenetrating polymer networks including synthetic polymers and which can form polycomplexes by interaction of positive and negative charges between the interpenetrating polymers include: poly(acrylic acid)/poly(methacrylamidopropyl-trimethyl-ammonium-chloride(MAPTAC))/water; poly(acrylic acid)/poly(allylamide)/water; poly(styrene-sulfonate)/poly(allylamide)/water; etc.

Examples of natural polymers suitable for forming interpenetrating polymer networks include: poly(glutamic acid); chitosan; poly(lysine); gelatin; deoxyribonucleic acid; and agarose. Examples of phase-transition gels which can exhibit a phase transition by interaction of positive and negative charges between interpenetrating polymers include: poly(glutamic acid)/chitosan/water; poly(glutamic acid)/poly(lysine)/water; etc. Examples of phase-transition gels which can exhibit a phase transition by hydrogen bonding between the interpenetrating polymers include: gelatin/gelatin/water; deoxyribonucleic acid(single strand)/deoxyribonucleic acid(single strand)/water; agarose/agarose/water; etc.

The polymers of the interpenetrating polymer network can be suitably treated to cause a significantly large volume change of the gel at a desired phase-transition condition in response to a stimulus. For example, the interpenetrating polymer network can be ionized in an amount sufficient to cause a significantly large volume change at a desired phase-transition condition. Other examples of treatment of the interpenetrating polymer network include oxidizing, reducing, complexing and chemically reacting the interpenetrating polymer network to cause a phase-transition at a desired phase-transition condition. An example of a phase-transition gel which can exhibit a significantly large volume change by reduction and oxidation includes an interpenetrating polymer network having interpenetrating polymers of poly(vinyl hydroquinone) and an acid solution as the liquid medium.

In a preferred embodiment, one or more of the polymers is at least partially ionized. For example, at least a portion of the acrylic acid groups in an interpenetrating network of poly(acrylimide) and poly(acrylic acid) are ionized. In a particularly preferred embodiment, a poly(acrylic acid) is ionized in an amount in the range of between about 0.01 percent and 10 percent of the acrylic acid groups of the poly(acrylic acid).

Phase-transition conditions at which the phase-transition gels exhibit a significantly large volume change can include physical conditions, chemical conditions, or combinations of physical and chemical conditions. Examples of physical phase-transition conditions include: temperature; electromagnetic radiation, such as infrared energy, visible light and ultraviolet light; etc. Examples of chemical phase-transition conditions include: concentration of ionic species, such as hydrogen and water, i.e. pH; crosslinking agents, such as cross-linking agents which crosslink the polymer network of the phase-transition gel; inorganic and organic solvents; specific chemicals; etc. Phase-transition conditions at which the phase-transition gels exhibit a significantly large volume change can include combinations of physical conditions, combinations of chemical conditions, or combinations of physical and chemical conditions.

The phase-transition gels of this invention can exhibit a significantly large volume change at a desired condition by causing a change in the binding of one polymer network of the interpenetrating polymer network in an amount sufficient to cause a significantly large volume change of the gel at a desired phase transition condition. For example, the amount of ionization of an ionized polymer within the interpenetrating polymer network can be selected to cause a significantly large volume change of the gel at a temperature that is different from the temperature that the gel would exhibit a significantly large volume change in the absense of ionization of the polymer.

Figure 1:
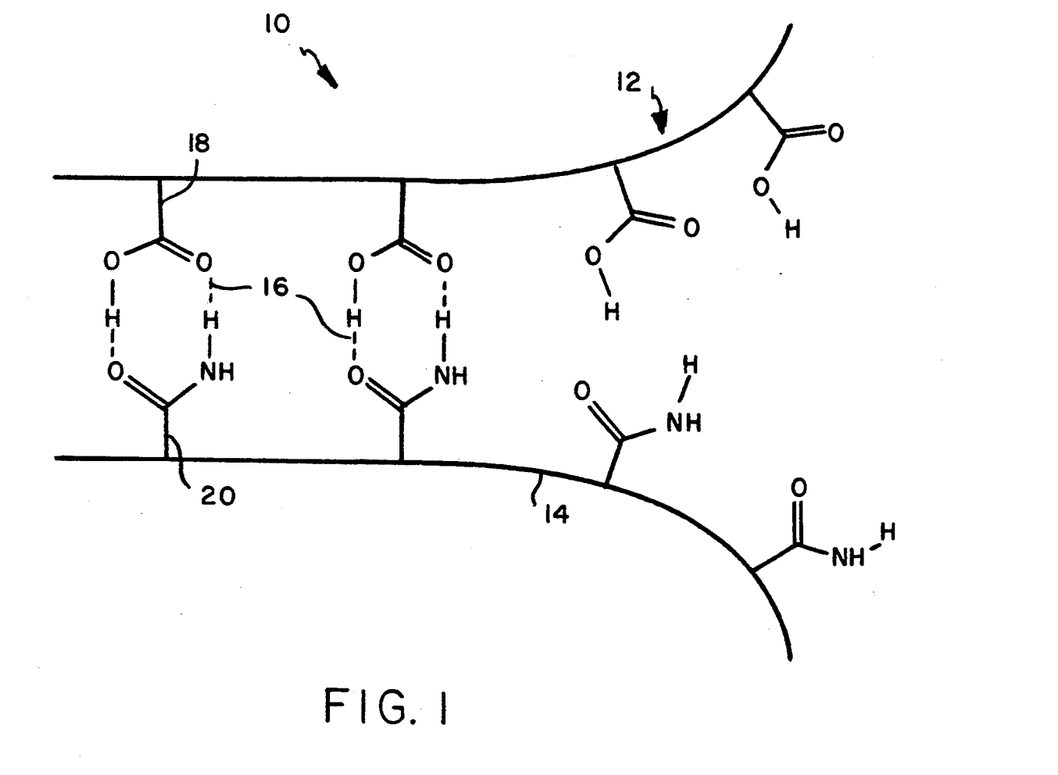
FIG. 1 is a schematic representation of polycomplexation between interpenetrating polymer networks of the present invention.

As illustrated in FIG. 1, polycomplexation of an interpenetrating polymer network 10 of a phase-transition gel comprising of poly(acrylic acid) 12 and poly(acrylamide) 14 can occur by the formation of hydrogen bonds 16 between acrylic acid groups 18 of the poly(acrylic acid) 12 and acrylimide groups 20 of the poly(acrylimide) 14, whereby an alignment, or polycomplexation, between the polymers occurs, thereby causing a significantly large volume change of the phase-transition gel.

It is to be understood that the interpenetrating polymer network can be designed to exhibit a phase transition in response to various types of interactions between a component in the liquid medium in the gel and either or both of the polymers of the interpenetrating polymer network. Examples of interactions between a component in a liquid medium and an interpenetrating polymer network or a polymer of an interpenetrating polymer network include van der Waals interaction, hydrophobic interaction, hydrogen bonding and ionic interaction. Interaction between the component and a polymer of the interpenetrating polymer can cause the polymer to exhibit a phase transition which, in turn, causes the interpenetrating polymer network to exhibit a phase transition. For example, a phase-transition gel including an interpenetrating polymer network of poly(acrylic acid) and poly(acrylamide) gelled with water, or an interpenetrating polymer network of interpenetrating polymers of poly(acrylic acid) gelled in water respond to changes in pH, ionic composition or solvent composition.

In another example, individual polymers of an interpenetrating polymer network can exhibit a phase transition in response to a physical change in the medium, such as temperature. The phase transition of the polymer can be caused by, for example, van der Waals forces, hydrophobic interaction, hydrogen bonding or ionic interaction within the polymer. Phase transition of the polymer, in turn, causes the interpenetrating polymer network to exhibit a phase transition.

Figure 2:
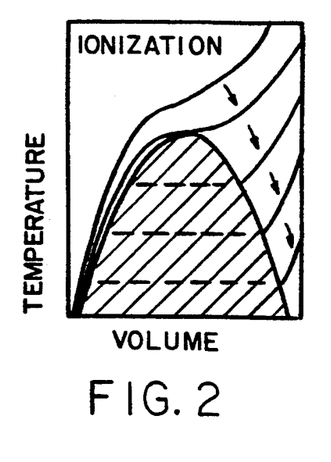
FIG. 2 is a plot of phase transitions for acrylamide gels in a solution of acetone and water wherein the gels have been ionized in varying degrees and wherein the phase transitions are a result of van der Waals interaction within the gels. The shaded area represents a region of discontinuous volume change of the gel. The dotted lines represent discontinuities in the phase state of a given polymer with a fixed ionization.
Figure 3:
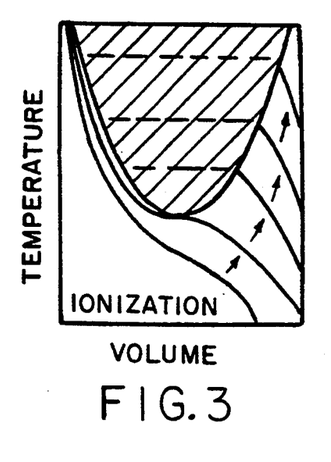
FIG. 3 is a plot of phase transitions for N-isopropylacrylamide gels in water wherein the gels have been ionized in varying degrees and wherein the phase transitions are a result of hydrophobic interaction within the gels. The shaded area represents a region of discontinuous volume change of the gel. The dotted lines represent discontinuities in the phase state of a given polymer with a fixed ionization.
Figure 4:
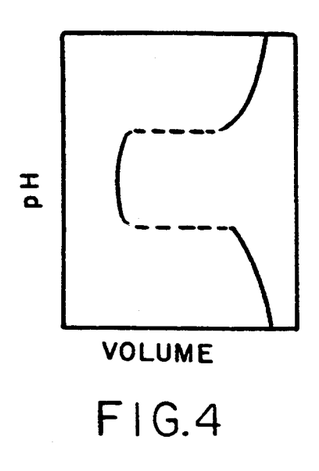
FIG. 4 is a plot of phase transition for acrylamide-sodium acrylate/methacrylamido-propyl-trimethylammonium chloride gel in water caused by ionic interaction within the gel in response to change of the pH of the water.

FIG. 2 is a plot of phase transitions for acrylamide gels in a solution of acetone and water wherein the gels have been ionized in varying degrees and wherein the phase transitions are a result of van der Waals interaction within the gels. FIG. 3 is a plot of phase transitions for N-isopropylacrylamide gels in water wherein the gels have been ionized in varying degrees and wherein the phase transitions are a result of hydrophobic interaction within the gels. FIG. 4 is a plot of phase transition for acrylamide-sodium acrylate/methacrylamidopropyltrimethylammonium chloride gel in water caused by ionic interaction in the gel in response to change of the pH of the water. FIGS. 2, 3 and 4 all represent examples of interactions within polymers of gels which cause the gels to exhibit phase transition. Formation of interpenetrating polymer networks which include these polymers can allow the consequent interpenetrating polymer network to also exhibit a phase transition. An example of one such gel includes a interpenetrating polymer network of poly(N-isopropylacrylamide) and poly(acrylamide) gelled with water.

In another illustration of the invention, interpenetrating polymer networks can be formed wherein either or both of the polymers of the interpenetrating polymer network interact with a component of the liquid medium in the gel by van der Waals forces, hydrophobic interaction, hydrogen bonding or ionic bonding. The interaction with the component causes, in turn, interaction between the polymers of the interpenetrating polymer network by, for example, van der Waals forces, hydrophobic interaction, hydrogen bonding or ionic interaction. The interaction between polymers can be different than the interaction with the component in the liquid medium. For example, hydrogen bonding between a component of the liquid medium and a polymer of the interpenetrating polymer network can cause an ionic interaction between the polymers of the interpenetrating polymer network. The interaction between the polymers of the interpenetrating polymer network causes the interpenetrating polymer network to exhibit a phase transition.

In one embodiment, the interpenetrating polymer network includes poly(acrylic acid) as one polymer and poly(acrylamide) as another, interpenetrating, polymer, and water as the liquid medium. In another embodiment, the interpenetrating polymer network includes two interpenetrating polymers of poly(acrylic acid) and water, as the liquid medium. Other examples include: poly(acrylic acid)/poly(methacrylamidopropyl-trimethyl-ammonium-chloride(MAPTAC)/water; poly(acrylic acid)/poly(allylamide)/water; poly(styrene-sulfonate)/poly(allylamide)/water; etc. Examples of phase-transition gels including interpenetrating polymer networks formed of natural polymers include: gelatin/gelatin/water; deoxyribonucleic acid(single strand)-/deoxyribonucleic acid(single strand)/water; agarose/agarose/water; etc.

Figure 5:
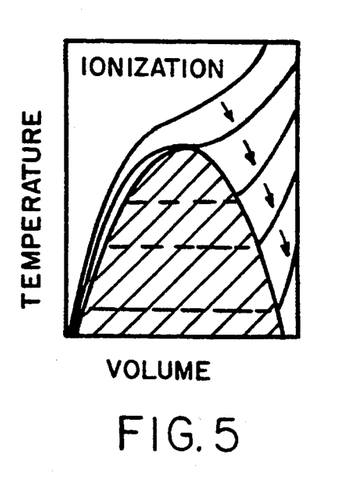
FIG. 5 is a plot of phase transitions for interpenetrating polymer network gels of poly(acrylic acid) and poly(acrylamide) in water wherein the gels have been ionized in varying degrees and wherein the phase transitions are a result of hydrogen bonding between the interpenetrating polymers. The shaded area represents a region of discontinuous volume change of the gel. The dotted lines represent discontinuities in the phase state of a given polymer with a fixed ionization.

In still another illustration of the invention, an interpenetrating polymer network can be formed which exhibits a phase transition in response to a change in the liquid medium, such as a temperature change. The temperature change causes an interaction between the polymers of the interpenetrating polymer network, such as van der Waals forces, hydrophobic interaction, hydrogen bonding or ionic interaction. The interaction between the polymers causes the interpenetrating polymer network to exhibit phase transition. FIG. 5 is a plot of phase transitions for an interpenetrating polymer network gels of poly(acrylic acid) and poly(acrylamide) in water wherein the gels have been ionized in varying degrees and wherein the phase transitions are a result of hydrogen bonding between the interpenetrating polymers.

The present invention has many applications. For example, the gel can interact with a body surface, such as the gut or skin. The gel can selectively absorb or release materials in the gut in response to specific environmental changes. Hormones, enzymes and other biotechnology products could be protected from destruction in the stomach if they were contained in a gel that was coated with an interpenetrating polymer network that was collapsed at low pH. For instance, oral insulin can be protected from being dissolved in the stomach by swelling insulin into a gel or a suitable medium which is then coated with an interpenetrating polymer network phase-transition gel that responds to pH. If the interpenetrating polymer network is designed to be in a contracted phase at low pH, then the insulin is protected when the polymer passes through the stomach. When the polymer and insulin reach the intestine, where the pH is relatively high, the interpenetrating polymer network coating exhibits a phase transition wherein the coating expands, thereby allowing the insulin to dissolve out of the gel. Also, physiologically active proteins, such as erythropoeitin, can be protected in this manner. It is to be understood, however, that the body surface does not have to be the gut. Further, any type of molecule, not just pharmaceutical compounds, can be released this way.

In another application of the present invention, a phase-transition gel can be formed which, when disposed in the gastrointestinal tract, absorbs cholesterol from digesting food. The presence of a high level of cholesterol causes an interaction between the cholesterol and the phase-transition gel to thereby cause the gel to exhibit a significantly large expansion. Expansion of the gel, in turn, causes the gel to absorb the cholesterol, so that it is not absorbed through the gut wall.

An example of an interpenetrating polymer network phase-transition gel which would absorb cholesterol includes an interpenetrating polymer network of poly(acrylic acid) gelled with bile salts and water. In one embodiment, obesity could be controlled by the interpenetrating polymer network phase-transition gel by absorption of fat from the intestinal tract. Since these gels can be programmed to undergo a significantly large volume change, thirty grams of dietary fat could be removed with a small amount of material. By incorporating bile salts, cholesterol can be selectively absorbed and filtered from the system. Hydrogen bonding of the interpenetrating polymer network changes by absorbing cholesterol.

In still another example of the invention, a phase-transition gel can be formed which can selectively separate a chemical from a liquid medium passing through an interpenetrating polymer network of the phase-transition gel. The presence of the chemical to be separated from the liquid medium can cause an interaction with the interpenetrating polymer network which, in turn, causes a significantly large contraction of the interpenetrating polymer network. The chemical is thereby trapped by the phase transition gel and separated from the liquid medium passing through the gel. An example of a phase-transition gel which selectively separates a chemical from a liquid medium is a gel having an interpenetrating polymer network of poly(N-isopropylacrylamide) and poly(acrylic acid) gelled with water. This gel can selectively absorb surfactants and expand.

Interpenetrating polymer networks can be formed which exhibit a phase transition for absorbing liquids, such as urine and blood, containing relatively high concentrations of ions. For example, the gels can selectively absorb osmotic fluids having an ion concentration of up to about 150 mM. Such gels could be used in disposable diapers and sanitary napkins. At least one polymer of the interpenetrating polymer network is an acidic (or anionic) polymer network and at least one other polymer of the interpenetrating polymer network is a basic (or cationic) polymer. Incorporation of acidic and basic polymers into the interpenetrating polymer network causes ions in the absorbed liquid, such as sodium ions and chloride ions, to become bonded to the polymers, thereby reducing osmotic pressure caused by the ions and enabling phase transition for absorption of fluids containing relatively high concentrations of ions. One example of such a gel includes an interpenetrating polymer network of an anionic poly(acrylic acid) and a cationic poly(methacrylamidopropyl-trimethyl-ammonium-chloride) (poly(MAPTAC)) in water. This gel swells about tenfold in salt solutions having concentrations greater than about 100 mM. Another example of a suitable gel includes an interpenetrating polymer gel of poly(styrene sulfuric acid) and poly(MAPTAC).

It is to be understood, however, that any combination of acidic and basic polymers can be used.

An interpenetrating polymer network phase-transition gel can also be formed which is salt-selective. An example of such a gel is a gel having an interpenetrating polymer network including poly(N-isopropylacrylamide) and poly(acrylic acid) gelled in valinomycin and water, which selectively absorbs potassium ions and undergoes phase transition. A clinically more significant enhancement would involve polymerizing the ionophore into the polymer. The gel could be swallowed after a meal and would absorb a fraction of its weight. A patient that had adrenal insufficiency and high serum potassium might benefit by taking such a product. Likewise, a patient with high blood pressure who is on a salt-restricted diet could benefit from a sodium-absorbing gel. Also, a patient who has renal failure and high phosphate could benefit by a phosphate-absorbing gel.

Also, since interpenetrating polymer network gels can be designed to recognize hydrogen, hydrophobic interactions, ions, and van der Waals forces, it is conceivable that custom-engineered interpenetrating polymer network gels can be created to recognize specific molecules that have given sequences. An application of this would be a gel to absorb microbial toxins from a bacteria, toxin, virus or other microorganism that is causing diarrhea. By absorbing the toxin, the toxin would not be available to irritate the gastrointestinal tract.

The invention will now be further and specifically described by the following examples. All parts and percentages are by weight unless otherwise stated.

Exemplification

Three different gels were formed comprising interpenetrating polymer networks of poly(acrylamide) and poly(acrylic acid). The first gel, Gel 1, was formed without ionization of either polymer in the interpenetrating polymer network. Three percent and six percent respectively, of the acrylic acid groups in the poly(acrylic acid) of Gels 2 and 3 were ionized.

The interpenetrating polymer networks of all three gels were prepared by first preparing three poly(acrylamide) gels. Five grams of acrylamide and 0.133 grams of N,N'-methylenebisacrylamide, commercially available from Bio-Rad Laboratories, and 120 microliters tetramethylenediamine (accelerator), commercially available from Bio-Rad Laboratories, were dissolved in 100 ml of water to form an aqueous solution. One ml of four percent aqueous ammonium persulfate solution (initiator), commercially available from Mallinkrodt was combined with the degassed aqueous solution to form a reaction solution.

The reaction solution was transferred to a glass capillary tube having a length of twenty centimeters and an internal diameter of 0.1 mm. The reaction solution gelled in the capillary tube, whereby the monomer and crosslinking agent reacted to form three poly(acrylamide) gels. Following gellation, the poly(acrylamide) gels were removed from the capillary tubes, washed with water and dried.

Five grams of distilled acrylic acid, 0.133 grams of N,N'methylenebisacrylamide and 40 mg of four percent ammonium persulfate solution were dissolved in 100 ml of water to form an aqueous solution. Three glass capillary tubes having a length of twenty centimeters and an internal diameter of 0.1 mm were filled with the aqueous solution. An amount of sodium hydroxide was added to two of the glass capillaries in an amount sufficient to ionize three percent of the acrylic acid groups in one of the capillary tubes and six percent of the acrylic acid groups in the other capillary tube.

The three dried poly(acrylamide) gels were inserted into the capillary tubes containing the aqueous solutions. The poly(acrylamide) gels were thereby swollen with the aqueous solution of acrylic acid. Radical polymerization was then initiated by raising the temperature of the poly(acrylamide) gels and aqueous solutions to a temperature of about 60° C., thereby forming interpenetrating polymer networks of poly(acrylimide) and poly(acrylic acid). Gel 1 included poly(acrylic acid) which was not ionized. In Gel 2, the poly(acrylic acid) was three percent ionized. In Gel 3, the poly(acrylic acid) was six percent ionized. The three gels were removed from their respective capillary tubes and washed with water. All three gels were disposed in separate glass micropipettes having an internal diameter of one millimeter.

The size and shape of the gels in the micropipettes were monitored at different temperatures using a Model C1966 AVEC image processor, commercially available from Hamamatsu Photonics, Inc. Each gel was submerged in water in a micropipette. The temperature of the water in the gels was controlled to within 0.01° C. using circulating water at temperatures in the range of between 4° C. and 50° C.

Figure 6:
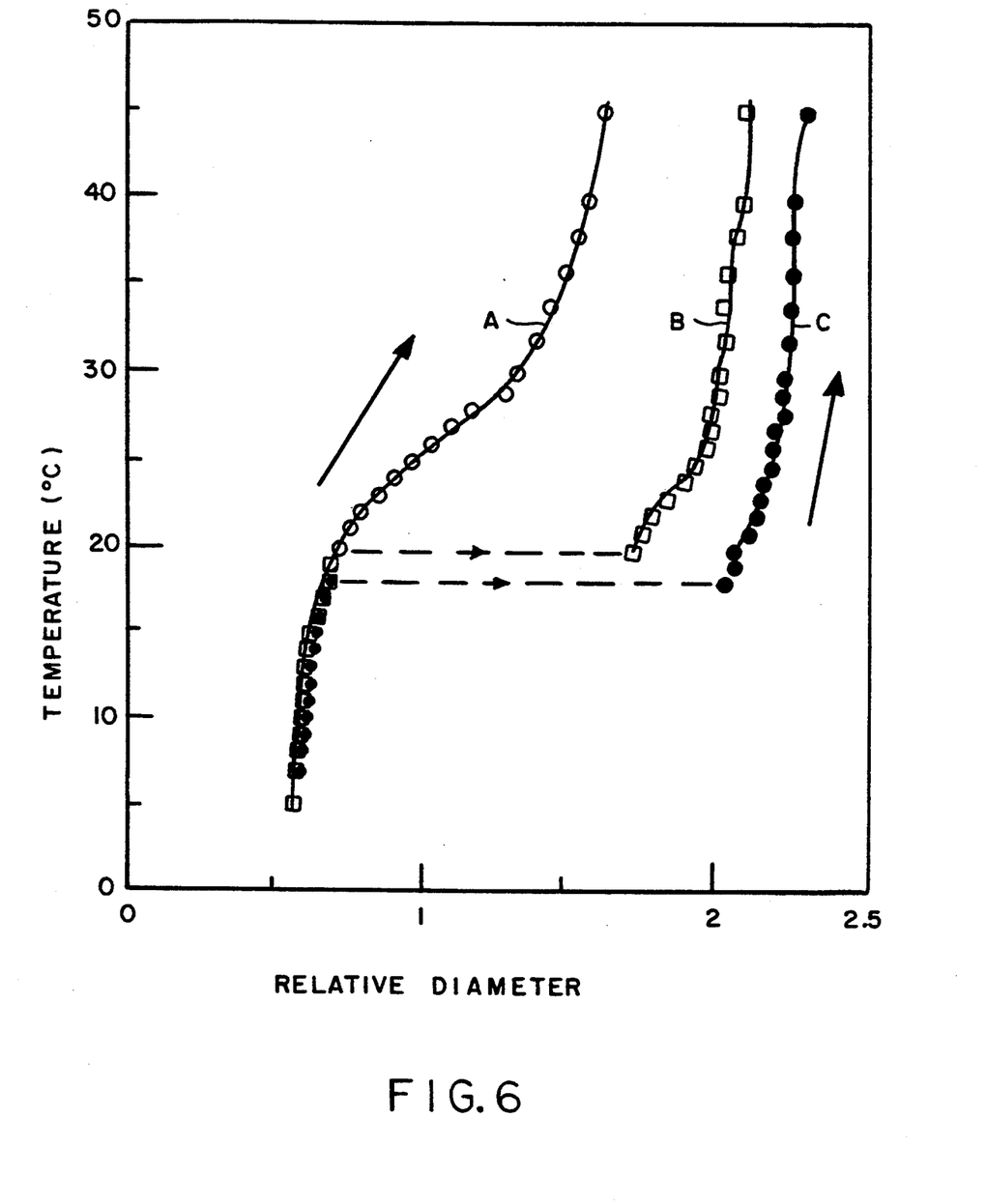
FIG. 6 is a plot of the volume of phase-transition gels of the present invention over a temperature range during phase transition from a contracted phase to an expanded phase.

FIG. 6 is a plot of the volume of Gel 1, Gel 2, and Gel 3 relative to their volumes in a contracted phase during expansion of the gels in response to an increase in temperature. Curve A represents the volume of Gel 1. As can be seen in Curve A, Gel 1 exhibits a continuous transition at a temperature in the range of between about 20° C. and 40° C. The volume change of Gel 2 and Gel 3, wherein the poly(acrylic acid) has been partially ionized, are represented by Curves B and C, respectively.

As can be seen from Curves B and C, Gel 2 and Gel 3 undergo phase transition during an increase in temperature. Gel 2 expands discontinuously at a temperature of about 20° C. Gel 3 exhibits a significantly large expansion at a temperature of about 18° C. The phase transition is a signficantly large expansion of the gels during a rise in temperature of the water in which the gels are submerged.

Also, as can be seen in Curves B and C, Gel 3 exhibits a phase transition at a temperature slightly lower than the phase transition of Gel 2. The temperature at which phase transition occurs therefore decreases with an increasing amount of ionization of the poly(acrylic acid) polymer in the interpenetrating polymer network of the phase-transition gel.

Figure 7:
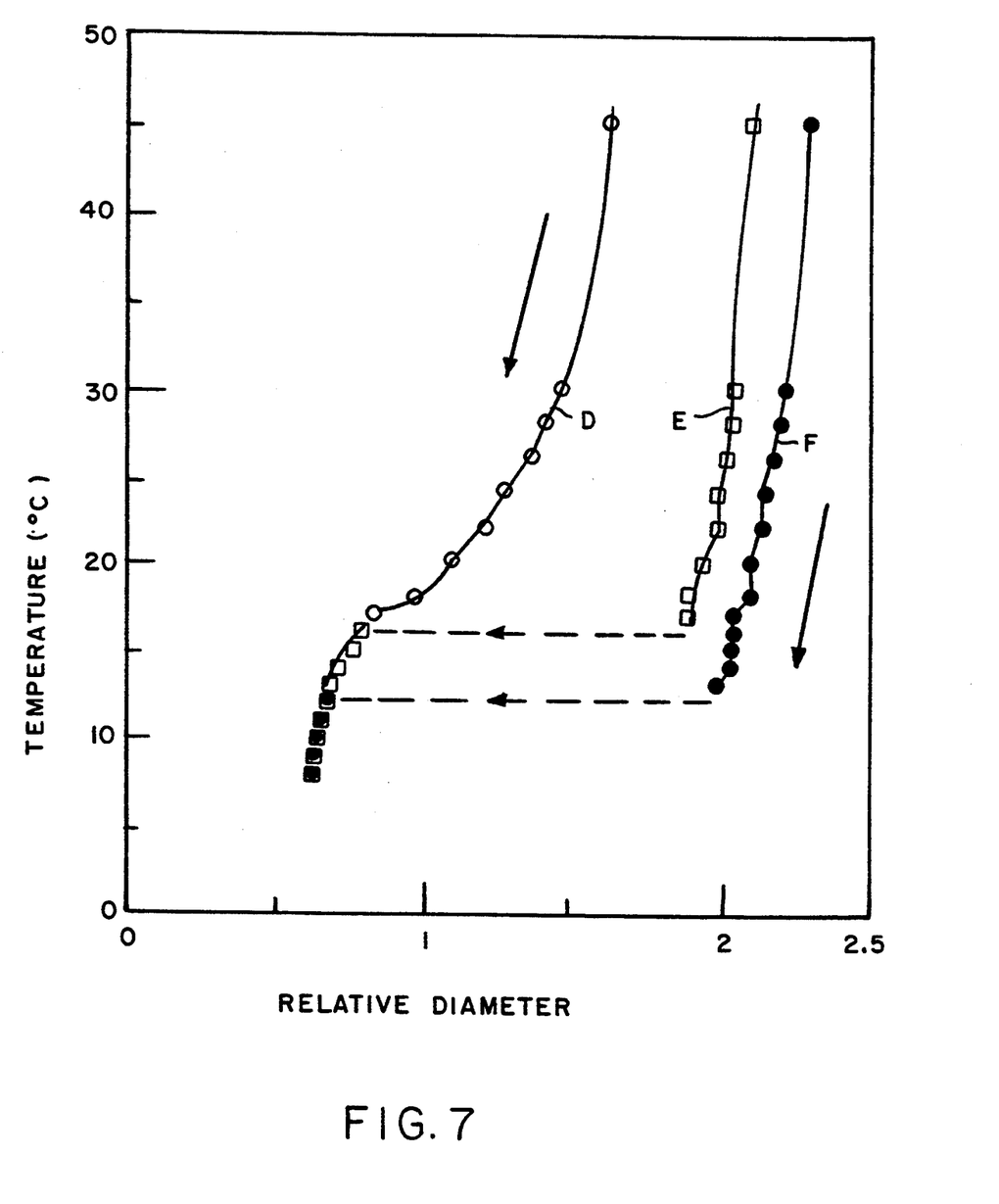
FIG. 7 is a plot of the volume of phase-transition gels of the present invention over a temperature range during phase transition from an expanded phase to a contracted phase.

FIG. 7 is a plot of the volume of Gel 1, Gel 2, and Gel 3 during contraction of the gels as the temperature of the water in which the gels are submerged is lowered. Gel 1, in which the poly(acrylic acid) polymer is not ionized, exhibits a continuous volume change in a temperature in the range of between 40° C. and about 20° C. Curve D represents the volume change of Gel 1, relative to the volume of Gel 1 in a contracted phase.

Curves E and F represent the volume change of Gel 2 and Gel 3, respectively, during contraction of Gel 2 and Gel 3. Gel 2 exhibits a significantly large contraction at a temperature of about 15° C. Gel 3 exhibits a significantly large contraction at a temperature of about 12° C. As with expansion, the temperature of significantly large contraction decreases with an increasing amount of ionization of the acrylic acid groups of the poly(acrylic acid) in the interpenetrating polymer network of the phase-transition gel.

Figure 8:
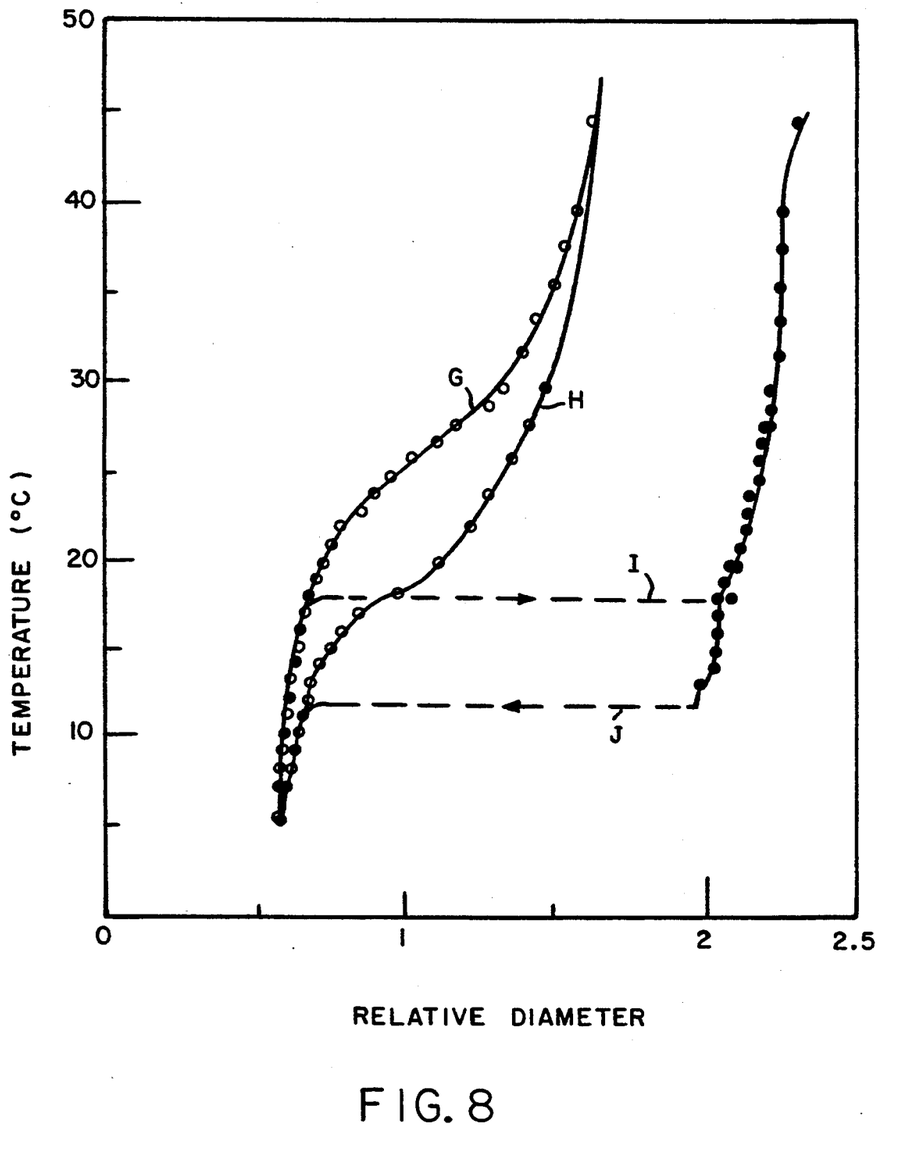
FIG. 8 is a plot of the volume of phase-transition gels of the invention having different amounts of ionization and demonstrating hysteresis between significantly large expansion and significantly large contraction of the gels.

FIG. 8 is a plot of the volume of Gel 1 and Gel 3 during expansion and contraction of the gels during a change of temperature of the water in which the gels are submerged. The volume of the gels are measured relative to the volume of the gels in the contracted state. Curve G represents the volume of Gel 1 during expansion of the gel as the temperature of the water is increased. Curve H represents the volume of Gel 1 during contraction of the gel as the temperature of the water is lowered. As can be seen from Curves G and H, Gel 1 exhibits hysteresis, wherein the volume of Gel 1 is different at given temperatures according to whether the gel is expanding or contracting.

Curve I represents the volume of Gel 3 during expansion of the gel. Curve J represents the volume of Gel 3 during contraction of the gel. As can be seen from Curves I and J, hysteresis of Gel 3 is exhibited during phase transition. The amount of hysteresis is more pronounced in Gel 3, which exhibits a phase transition than in Gel 1 which exhibits only a continuous volume change over the same temperature range.

Equivalents

Those skilled in the art will recognize, or be able to ascertain using no more than routine experimentation, many equivalents to the specific embodiment of the invention described specifically herein. Such equivalents are intended to be encompassed in the scope of the following claims.

We claim:

1. A composition of matter, comprising: a polymer gel that includes at least one polymer interpenetrating at least a second polymer, the gel capable of undergoing a reversible, continuous or discontinuous phase transition in response to a change in a specific stimulus applied to the gel.

2. The composition of claim 1, wherein said phase-transition is initiated by a change in at least one of temperature, pH, solvent concentration, light irradiation, electric field strength and ion concentration.

3. The composition of claim 1, wherein said gel undergoes a discontinuous phase-transition collapse in response to the change in the specific stimulus.

4. A composition of matter, comprising:
an interpenetrating polymer network gel including at least a first polymer interpenetrating at least a second polymer, said polymers arranged with respect to each other so that at least one type of interaction develops between at least the first and second polymers, the at least one type of interaction sufficient to cause the gel to undergo a phase-transition in response to a change in a stimulus applied to the gel.

5. The composition of claim 4, wherein the at least one type of interaction is selected from the group consisting of van der Waals forces, hydrophobic interactions, hydrogen bonding, and ionic interactions.

6. The composition of claim 5, wherein the hydrogen bonding between said at least first and second polymers allows said polymers to form a polycomplex in which said polymers are aligned, polycomplex formation sufficient to induce said gel to undergo a discontinuous phase transition.

7. The composition of claim 4, wherein said change in stimulus is a change in temperature from a higher temperature to a lower temperature sufficient to cause the gel to undergo a phase-transition collapse in response to the change in temperature applied to the gel.

8. A gel network capable of undergoing a continuous or discontinuous phase-transition in response to a change in a stimulus, the gel comprising:
an interpenetrating network of at least a first polymer and at least a second polymer, said polymers interpenetrating in a manner that results in an attractive interaction between the polymers of said network; wherein said attractive interaction is sufficient to cause the gel network to undergo phase-transition in response to a change in stimulus applied to the gel.

9. The gel of claim 8, wherein said interpenetrating polymers are arranged to result in hydrogen bonding between said at least first and second polymers.

10. The gel of claim 9, wherein at least said first polymer is ionized.

11. The gel of claim 10, wherein ionization of at least one of said first or second polymers is directly related to the phase transition, such that a larger degree of ionization effects a discontinuous phase transition, and a smaller degree of ionization effects a continuous phase transition.

12. The gel of claim 11, wherein said at least first polymer is polyacrylic acid and said second polymer is polyacrylamide.

13. The gel of claim 12, wherein said first polymer is not ionized and said gel undergoes a continuous phase transition collapse in response to a decrease in temperature.

14. The gel of claim 12, wherein said first polymer is ionized to greater than about 3 percent and said gel undergoes a discontinuous phase transition collapse in response to a decrease in temperature.

15. The gel of claim 8, further comprising a chemical incorporated into the gel network, said chemical capable of being released from the gel network upon a phase-transition collapse in response to a change in stimulus applied to the gel network.

16. A method for incorporating a material into a gel, comprising the steps of:
providing an interpenetrating polymer gel network including at least a first polymer interpenetrating at least a second polymer, said polymers arranged with respect to each other so that at least one type of interaction develops between at least the first and second polymers, the at least one type of interaction sufficient to cause the gel to undergo a phase-transition expansion in response to a change in a stimulus applied to the gel;
contacting the gel network with the material;
changing the specific stimulus such that the gel network undergoes phase-transition expansion, thereby incorporating the material into the gel network.

17. A method for releasing a material from a gel, comprising the steps of:
providing an interpenetrating polymer gel network including the material and at least a first polymer interpenetrating at least a second polymer, said polymers arranged with respect to each other so that at least one type of interaction develops between at least the first and second polymers, the at least one type of interaction sufficient to cause the gel to undergo a phase-transition collapse in response to a change in a stimulus applied to the gel; changing the specific stimulus such that the gel network undergoes a phase-transition collapse, thereby releasing the material from the gel.

18. In a polymer, wherein the improvement comprises:
at least a first polymer and at least a second polymer, said polymers arranged with respect to each other so that at least one type of interaction develops between at least the first and second polymers, the at least one type of interaction sufficient to cause the gel to undergo a continuous or discontinuous phase-transition in response to a change in a stimulus applied to the gel.

19. The polymer of claim 18, wherein said phase-transition is initiated by a change in at least one of temperature, pH, solvent concentration, light irradiation, electric field strength and ion concentration.

20. The polymer of claim 18, wherein the interaction is hydrogen bonding between said at least first and second polymers, said hydrogen bonding allowing said polymers to form a polycomplex in which said polymers are aligned, polycomplex formation sufficient to induce said gel to undergo a discontinuous phase transition in response to a change in stimulus applied to the gel.

21. The polymer of claim 20, wherein said change in stimulus is a change in temperature.

22. The polymer of claim 20, wherein said at least first polymer is polyacrylic acid and said second polymer is polyacrylamide.

23. A method of releasing a material in response to a change in stimulus comprising the steps of:
introducing the material into a medium;
coating the medium with a polymer gel that includes at least one polymer interpenetrating at least a second polymer, the gel being capable of undergoing a reversible phase transition in response to the change in stimulus applied to the gel; and
changing the stimulus such that the gel coating expands and the material is released.

24. The method of claim 23, wherein the step of changing the stimulus comprises increasing pH.

25. The method of claim 23, wherein the step of introducing the material comprises introducing insulin.

26. The method of claim 24, wherein the step of changing the stimulus comprises exposing the coated medium to an intestine.

27. A method of absorbing a compound comprising the steps of:
providing a polymer gel that includes at least one polymer interpenetrating at least a second polymer, the gel being capable of undergoing a reversible phase transition when contacted with the compound; and
contacting the gel with the compound such that the gel expands and absorbs the compound.

28. The method of claim 27, wherein the step of contacting the gel with the compound comprises contacting with cholesterol.

29. A method of separating a compound from a liquid medium comprising the steps of:
providing a polymer gel that includes at least one polymer interpenetrating at least a second polymer, the gel being capable of undergoing a reversible phase transition when contacted with the compound;
contacting the gel with a liquid solution containing the compound such that the gel contracts and the compound is retained within the gel.

30. The composition of claim 4, wherein said change in stimulus is a change in at least one of temperature, pH, solvent concentration, light irradiation, electric field strength and ion concentration.

31. The composition of claim 4, wherein said interpenetrating polymer network gel undergoes a discontinuous phase-transition collapse in response to the change in the specific stimulus.

32. The gel of claim 9, wherein said hydrogen bonding interaction between the first and second polymers increases hydrophobicity of said polymer network.

33. A method of releasing a material in response to a change in stimulus comprising the steps of:
introducing the material into a medium;
coating the medium with a polymer gel that includes at least one polymer interpenetrating at least a second polymer, said polymers arranged with respect to each other so that at least one type of interaction develops between at least the first and second polymers, the at least one type of interaction being sufficient to cause the gel to undergo a phase transition in response to the change in stimulus applied to the gel; and
changing the stimulus such that the gel coating expands and the material is released.

34. The method of claim 33, wherein the step of introducing the material comprises increasing pH.

35. The method of claim 33, wherein the step of introducing the material comprises introducing insulin.

36. The method of claim 34, wherein the step of changing the stimulus comprises exposing the coated medium to an intestine.

37. A method of absorbing a compound comprising the steps of:
providing a polymer gel that includes at least one polymer interpenetrating at least a second polymer, said polymers arranged with respect to each other so that at least one type of interaction develops between at least the first and second polymers, the at least one type of interaction sufficient to cause the gel to undergo a phase transition when contacted with the compound; and
contacting the gel with the compound such that the gel expands and absorbs the compound.

38. The method of claim 36, wherein the step of contacting the gel with the compound comprises contacting with cholesterol.

39. A method of separating a compound from a liquid medium comprising the steps of:
providing a polymer gel that includes at least one polymer interpenetrating at least a second polymer, said polymers arranged with respect to each other so that at least one type of interaction develops between at least the first and second polymers, the at least one type of interaction being sufficient to cause the gel to undergo a phase transition when contacted with the compound;
contacting the gel with a liquid solution containing the compound such that the gel contracts and the compound is retained within the gel.

* * * * *